United States Patent [19]
Loeffler

[11] Patent Number: 5,897,911
[45] Date of Patent: Apr. 27, 1999

[54] POLYMER-COATED STENT STRUCTURE

[75] Inventor: Joseph P. Loeffler, Mountain View, Calif.

[73] Assignee: Advanced Cardiovascular Systems, Inc., Santa Clara, Calif.

[21] Appl. No.: 08/909,399

[22] Filed: Aug. 11, 1997

[51] Int. Cl.[6] .............................. B05D 3/12; B05D 7/22
[52] U.S. Cl. ..................... 427/2.25; 427/2.3; 427/2.28
[58] Field of Search .................... 427/2.3, 2.24, 427/2.25, 2.28, 358

[56] References Cited

U.S. PATENT DOCUMENTS

| | | | |
|---|---|---|---|
| 4,731,073 | 3/1988 | Robinson | 623/1 |
| 5,059,169 | 10/1991 | Zilber | 604/8 |
| 5,141,494 | 8/1992 | Danforth et al. | 604/96 |
| 5,163,958 | 11/1992 | Pinchuk | 623/11 |
| 5,234,457 | 8/1993 | Andersen | 606/198 |
| 5,370,684 | 12/1994 | Vallana et al. | 623/1 |
| 5,389,108 | 2/1995 | Tower | 606/198 |
| 5,401,257 | 3/1995 | Chevalier, Jr. et al. | 604/265 |
| 5,449,382 | 9/1995 | Dayton | 623/1 |
| 5,534,287 | 7/1996 | Lucik | 427/2.25 |
| 5,537,729 | 7/1996 | Kilobow | 427/2.3 |
| 5,624,411 | 4/1997 | Tuch | 604/265 |
| 5,630,840 | 5/1997 | Mayer | 623/1 |
| 5,632,779 | 5/1997 | Davidson | 623/12 |
| 5,693,085 | 12/1997 | Buirge et al. | 623/1 |
| 5,700,285 | 12/1997 | Myers et al. | 623/1 |
| 5,749,880 | 5/1998 | Banas et al. | 606/198 |
| 5,772,864 | 6/1998 | Moller et al. | 205/73 |
| 5,800,522 | 9/1998 | Campbell et al. | 623/1 |
| 5,837,313 | 11/1998 | Ding et al. | 427/2.25 |

FOREIGN PATENT DOCUMENTS

| | | |
|---|---|---|
| 0 621 015 | 10/1994 | European Pat. Off. . |
| 0 627 226 | 12/1994 | European Pat. Off. . |
| 0 701 802 | 3/1996 | European Pat. Off. . |
| WO 93 06781 | 4/1993 | WIPO . |
| WO 95/11817 | 5/1995 | WIPO . |
| WO 96/28115 | 9/1996 | WIPO . |

*Primary Examiner*—Diana Dudash
*Attorney, Agent, or Firm*—Fulwider Patton Lee & Utecht, LLP

[57] ABSTRACT

The thickness of a polymer coating applied to the interior surface of a stent is precisely controlled by fitting a mandrel within its interior. Fitment of an exterior mold serves to additionally control the thickness of polymer on the exterior surface of the stent. Alternatively, a preformed sheath of polymer is fitted to the interior of the stent whereby the subsequent application of polymer not only causes the exterior to become coated but also causes the sheath to become adhered to the stent.

21 Claims, 1 Drawing Sheet

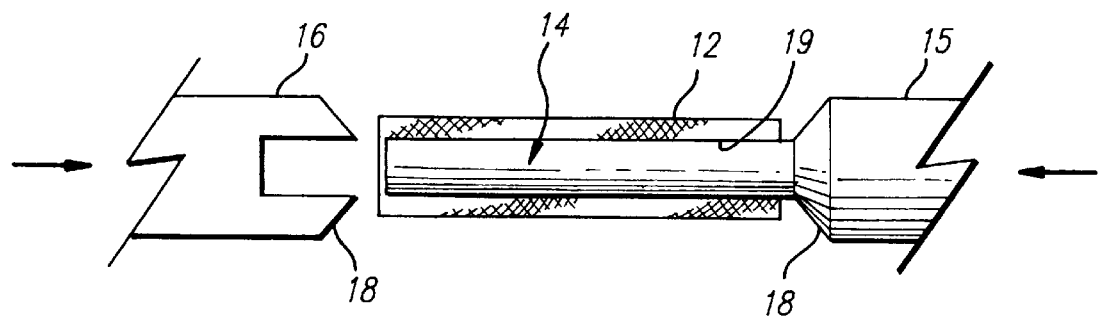
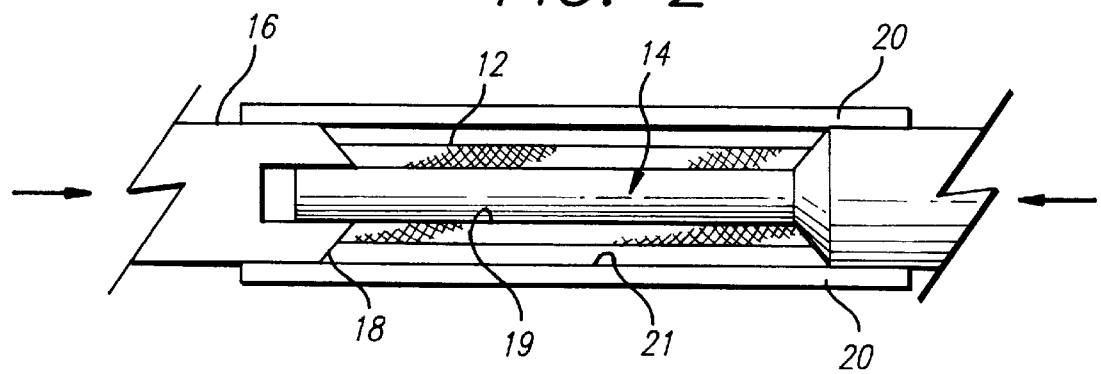
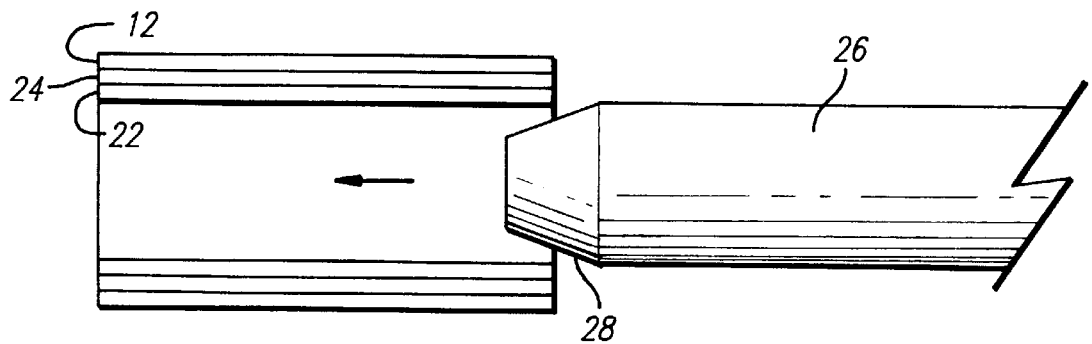

POLYMER-COATED STENT STRUCTURE

BACKGROUND OF THE INVENTION

This invention relates generally to expandable intraluminal vascular grafts, commonly referred to as stents, and more particularly concerns the coating of metal stents with polymer materials capable of carrying and releasing therapeutic drugs.

Stents are implanted within vessels in an effort to maintain the patency thereof by preventing collapse and/or by impeding restenosis. Implantation of a stent is typically accomplished by mounting the stent on the expandable portion of a balloon catheter, maneuvering the catheter through the vasculature so as to position the stent at the desired location within the body lumen, and inflating the balloon to expand the stent so as to engage the lumen wall. The stent automatically locks into its expanded configuration allowing the balloon to be deflated and the catheter removed to complete the implantation procedure.

It is often desirable to provide localized pharmacological treatment of a vessel at the site being supported by the stent and it has been found convenient to utilize the stent as a delivery vehicle for such purpose. However, because of the mechanical strength that is required to properly support vessel walls, stents must typically be constructed of metallic materials which are not capable of carrying and releasing drugs. Various polymers on the other hand are quite capable of carrying and releasing drugs but generally do not have the requisite mechanical strength. A previously devised solution to such dilemma has been the coating of a stent's metallic structure with a polymer material in order to provide a stent capable of both supporting adequate mechanical loads as well as delivering drugs.

Various approaches have previously been used to join polymers to metallic stents including dipping, spraying and conforming processes. However, such methods have failed to provide an economically viable method of applying a very even coating of polymer on the stent surfaces or the ability to economically apply different thicknesses or different polymers in different areas on the same stent.

The prior art has been unable to overcome such shortcomings and a new approach is needed for effectively and economically applying a polymeric material to a metallic stent with a high degree of precision.

SUMMARY OF THE INVENTION

The present invention provides a method of joining a polymeric material with a metallic stent that overcomes the disadvantages and shortcomings of previously employed processes. More particularly, by such method, very precisely controlled thicknesses of polymer can be applied to selected surfaces of a stent. The resulting stent has the mechanical strength necessary to properly support a blood vessel while being capable of delivering a preselected quantity of drug or drugs over a desired period of time. Moreover, the attached polymer does not interfere in the deployment of the stent and therefore allows the stent to be freely expanded.

The methods of the present invention call for the use of mandrels and/or molds to apply precise amounts of polymer to the stent surfaces. Moreover, advantageous positioning of such implements relative to the stent allow the thickness of the polymer to be varied from surface to surface. It is thereby readily possible to apply a thicker layer of polymer to the blood-facing side of the stent than to the vessel-facing side or vice versa. Additionally, by employing successive molding operations, different polymers, selected for their differentiated ability to absorb and release different therapeutic agents, can be applied to selected surfaces of the stent. Alternatively, the polymer may be applied to one side of the stent as a preformed sheath, while the subsequent molding operation not only serves to coat the opposite surface of the stent but also serves to adhere the preformed sheath to the stent as well. Upon implantation of such stent with differentiated surfaces it is thereby possible to directly expose the vessel wall to one therapeutic agent while the blood is exposed to a different therapeutic agent. Alternatively, it is possible to load polymers with different carrying capacities of a particular therapeutic agent to thereby deliver different concentrations in a desired pattern.

The method of the present invention includes a number of alternative embodiments including the use of various combinations of mandrel configurations, and exterior molds. The polymer is applied by either a dip coating, pultrusion or injection molding process. The methods of the present invention ensure that very precisely dimensioned coatings result even after the drying and the cooling processes are completed. A final serration or separation step may be necessary for some stent configurations in order to restore the desired flexibility and expendability to the stent. A laser is used for such purpose to quickly and precisely cut and/or remove polymer from various locations on the coated stent.

These and other features and advantages of the present invention will become apparent from the following detailed description of a preferred embodiment which, taken in conjunction with the accompanying drawings, illustrates by way of example the principles of the invention.

BRIEF DESCRIPTION OF THE DRAWINGS

FIG. 1 is a cross-sectional view of a mandrel being positioned within a stent.

FIG. 2 is a cross-sectional view of a mandrel in position within a stent and an exterior mold positioned thereabout.

FIG. 3 is a cross-sectional view of a mandrel being inserted into a preformed sheath containing stent.

DETAILED DESCRIPTION OF THE PREFERRED EMBODIMENTS

The figures generally illustrate the techniques used to apply polymer to a stent in accordance with the present invention. Any of a variety of stent configurations may be subjected to the coating process described herein including, but not limited to multi-link or slotted tube-type designs. The metals from which such stents are formed may include stainless steels, NiTi and tantalum among others. The polymer or a combination of polymers that are applied thereto are selected for their ability to carry and release, at a controlled rate, various therapeutic agents such as anti-thrombogenic or anti-proliferative drugs. The polymeric material of the invention preferably comprises a biodegradable, bioabsorbable polymeric film that is capable of being loaded with and capable of releasing therapeutic drugs. The polymeric materials preferably include, but are not limited to, polycaprolactone (PCL), poly-DL-lactic acid (DL-PLA) and poly-L-lactic acid (L-PLA) or lactide. Other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. Examples of non-degradable synthetic polymers are Parylene®, Parylast® (from Advanced Surface Technology of Billerica, Mass.), polyurethane, polyethylene, polyethylene teraphthalate, ethylene vinyl acetate, silicone and polyethylene oxide (PEO).

Examples of therapeutic drugs, or agents that can be combined with the polymeric materials include antiplatelets, anticoagulants, antifibrins, antithrombins, and antiproliferatives. Examples of antiplatelets, anticoagulants, antifibrins, and antithrombins include but are not limited to sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of cytostatic or antiproliferative agents include angiopeptin (a somatostatin analogue from Ibsen), angiotensin converting enzyme inhibitors such as Captopril® (available from Squibb), Cilazapril® (available from Hoffman-LaRoche), or Lisinopril® (available from Merck); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as to PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon and genetically engineered epithelial cells, for example.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agent are known in the art. Furthermore, the calculation of dosages, dosage rates and appropriate duration of treatment are previously known in the art.

FIG. 1 illustrates the method of the present invention in its simplest form. The stent 12 is first slipped onto a mandrel in the form of a core pin 14 after which a pin cap 16 is fitted to its distal end. The core pin extends from a proximal section 15 of increased diameter similar to the outer diameter of the pin cap. As these two pin components are advanced towards one another, the tapered configurations of the corresponding receiving surfaces 18 automatically cause the stent to become centered about the core pin. The interference fit between the core pin and pin cap ensures that the components remain assembled and properly aligned during subsequent handling and processing. The pin is precisely dimensioned to provide the desired spacing 19 between its exterior surface and the interior surface of the stent. Such fixation of the stent also serves to minimize the area of contact between the stent and mandrel, and is thereby limited to only two very narrow circles on the opposite edges of the stent.

The assembly is subsequently submersed in the selected polymer in its liquid or molten state. Adjustment of the viscosity of the polymer may be necessary in order to ensure free access to the space between the core pin and stent via the link spacings or slots. Such adjustment may be achieved either by thermal or chemical means and is best optimized by empirical methods as are well know in the art. The presence of the pin strictly limits and thereby precisely controls the maximum thickness of polymer that can be applied to the stent's interior surface. Moreover, prolonged or repeated contact with the polymer allows a substantially thicker layer of polymer to be built up on the exterior of the stent while the thickness of the interior layer remains constant. Alternatively, subsequent exposure to a second polymer allows the exterior, i.e. vessel side of the stent, to be coated with a different polymer than is attached to its interior, i.e. blood side. After the polymer or polymers have all solidified or sufficiently cured, the core pin and pin cap are removed.

As an alternative to the submersion or dipping technique, the core pin/stent assembly is fitted to the exit port of an extruder and the polymer is applied to the stent using a pultrusion technique well known in the art. Selection of the appropriate viscosity of the polymer is again critical not only to ensure perfusion of the polymer through openings in the stent and into the space between the stent and core pin but also to achieve adequate coverage.

FIG. 2 illustrates a further alternative embodiment of the present invention wherein an exterior mold is utilized in addition to the core pin described above. The stent 12 is again first mounted about the core pin 14 and pin cap 16 after which the entire assembly is fitted inside an external mold 20. The stent is thereby secured in position so as to define a precise spacing between the exterior of the core pin and the interior surface of the stent 19 and between the exterior surface of the stent and the interior of the external mold 21. Polymer is subsequently injected either via any number of routes including a passage extending through the core pin 14 or through the external mold 20. The viscosity of the polymer must be selected to facilitate its flow into the mold and through the stent to ensure that an uninterrupted coating of the stent is achieved. Conditions that affect the viscosity requirements include but are not limited to the anticipated temperatures, cooling rates, molding time, orifice sizes, molding pressure, and the metal from which the stent is formed, etc. The appropriate viscosity is easily selected by one skilled in the art using simple empirical techniques. After the polymer has solidified or sufficiently cured, the coated stent and core pin are removed from the mold as a unit after which the core pin and pin cap are removed from the stent. Successive molding operations with differently sized core pins or outer molds allow layers of different materials to be built up on either the internal or exterior surface of the stent.

An alternative embodiment obviates the use of the core pin and cap described above whereby a preformed polymer sheath is initially inserted into the stent. By subsequently applying polymer in its liquid state to the exterior of the stent, such sheath becomes joined to the applied polymer and thus the stent becomes completely encased in polymer. The preformed nature of the sheath serves to precisely define the thickness of polymer applied to the interior surface of the stent. A dip coating process sans exterior mold allows the polymer to be selectively built up on the exterior side of the stent while the use of an external mold positively limits its external thickness. The polymer from which the sheath is preformed does not necessarily have to correspond to the polymer that is subsequently applied in its flowable form, thus disparate types of polymer can be applied to the surfaces of the stent.

FIG. 3 illustrates the preferred method of practicing this embodiment. The polymer sheath 24 that is to comprise the inner surface of the finished product is first applied to a teflon or silicon support tube 22, either by dip coating or extrusion. The metal stent 12 is then slipped over such coated tube after which a tapered mandrel 26 is inserted thereunto. The taper 28 facilitates insertion and expands the polymer sheath snugly against the interior surface of the stent 12. The exterior of the stent is then coated with polymer either by dipping or pultrusion sans mold or by injection molding with the use of an external mold. After curing, the mandrel 26 and support tube 22 are removed to provide a fully coated stent.

Depending upon the type of stent structure to which the polymer is applied, it may be necessary to remove some of the polymer or at least cut the polymer at selected sites in order to restore the requisite flexibility to the stent. A multi-link stent for example necessarily requires that the various links are able to undergo relative movement during the expansion of the devices. The presence of polymer or at least the presence of a continuous mass of polymer between such links could inhibit relative movement and thus inhibit expansion of the stent during deployment. In order to remedy such effect it is necessary to either remove or at the very least, perforate the polymer in such locations. The preferred method of doing so is with the use of a laser with which polymer material can be quickly and precisely penetrated as required.

With certain stent configurations, it is advantageous to apply polymer to the stent while such stent is in its expanded state. The stent is initially expanded, such as by advancing the core pin and pin cap towards on another to force the stent sufficiently high up along the tapered surface to achieve its deployed diameter. Alternatively, an oversized sheath and mandrel may be used. Any of the various alternative embodiments described above may then be utilized to apply the polymer. Application of the polymer while the certain stent configurations are expanded result in less webbing between the struts and yields greater final mechanical stability. Additionally, the final polymer coating may need little or no laser processing for separation or clean up before the stent is contracted down to its pre-delivery O.D.

After the stent is coated and trimmed, therapeutic agent or agents are loaded at desired concentration levels per methods well known in the art to render the device ready for implantation.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A method for coating a stent, comprising the steps of:
    providing a stent having a generally cylindrical shape, said stent having an interior surface and an exterior surface;
    securely positioning a mandrel within said stent to define a space of substantially constant thickness between said mandrel and said interior surface of said stent;
    contacting said mandrel containing stent with a polymer in a flowable state;
    allowing said polymer to transform to a substantially non-flowable state; and
    removing said mandrel from said stent.

2. The method of claim 1, wherein said mandrel containing stent is contacted with said polymer so as to coat said exterior surface of said stent with a layer of polymer having a thickness that is greater than the thickness of said space between said mandrel and the interior surface of said stent.

3. The method of claim 1 wherein said stent is contacted with said polymer by submerging said stent in a mass of said polymer in its flowable state.

4. The method of claim 1 wherein said stent is contacted with said polymer by a pultrusion technique.

5. The method of claim 1 further comprising the step of re-contacting said mandrel containing stent with said polymer in said flowable state after said polymer with which said stent had previously been contacted has transformed to said substantially non-flowable state and prior to removal of said mandrel whereby said exterior and interior surfaces of said stent become differentiated in terms of the thickness of the polymer coatings thereon.

6. The method of claim 1, further comprising the step of contacting said stent with a second polymer in a flowable state after said first polymer has become transformed to a substantially non-flowable state and prior to removal of said mandrel whereby the exterior and interior surfaces of said stent become differentiated in terms of the polymers coated thereon.

7. The method of claim 1 wherein said mandrel comprises a core pin and pin cap, wherein said pin cap slidably receives the distal end of said core pin and wherein both said core pin and pin cap include a conical surface that extends to diameter greater than that of said stent, the method further comprising the step of advancing said pin cap along said core pin whereby the stent becomes coaxially secured in position relative to said core pin.

8. A method for coating a stent, comprising the steps of:
    providing a stent having a generally cylindrical shape, said stent having an interior surface and an exterior surface;
    securely positioning a mandrel within said stent to define a first space of a substantially constant first thickness between said mandrel and said interior surface of said stent;
    securely positioning said mandrel containing stent within an exterior mold to define a second space of a substantially constant second thickness between said exterior mold and said exterior surface of said stent;
    introducing a polymer in a flowable state into said first and second spaces;
    allowing said polymer to transform to a substantially non-flowable state; and
    removing said exterior mold from about said stent and said mandrel from within said stent.

9. The method of claim 8 and wherein said first thickness is greater than said second thickness.

10. The method of claim 9 wherein said second thickness is greater than said first thickness.

11. The method of claim 8 further comprising the steps of:
    removing only said exterior mold from about said stent after said polymer has transformed into a substantially non-flowable state;
    securely positioning said mandrel containing stent within a second exterior mold to define a third space between the exterior surface of said first polymer coated stent and said second exterior mold; and
    introducing a second polymer in a flowable state into said third space.

12. A method of coating a stent, comprising the steps of:
    providing a stent having a generally cylindrical shape, said stent having an interior surface and an exterior surface;
    fitting a sheath preformed of a first polymer within said stent;
    contacting said stent with a second polymer in a flowable state; and allowing said second polymer to transform into a substantially non-flowable state.

13. The method of claim 12 wherein said first and second polymers are the same.

14. The method of claim 12 wherein said first and second polymers are different.

15. The method of claim 12 further comprising the step of inserting a mandrel into said sheath of said first polymer fitted within said stent in order to expand said sheath of polymer against the interior surface of said stent.

16. The method of claim 15 where in said mandrel has a tapered tip.

17. The method of claim 12 further comprising the step of securely positioning said sheath containing stent within an exterior mold to define a space between the exterior surface of said stent and said mold having a constant first thickness.

18. The method of claim 17 where in said sheath of polymer has a constant second thickness and wherein said first and second thickness are equal.

19. The method of claim 17 wherein said cylinder of polymer has a constant second thickness and wherein said first and second thickness are not equal.

20. The method of claim 19 wherein said first thickness is greater than said second thickness.

21. The method of claim 19 wherein said second thickness is greater than said first thickness.

* * * * *